United States Patent
Jackson, III et al.

(10) Patent No.: US 6,930,314 B2
(45) Date of Patent: Aug. 16, 2005

(54) LIGHT DETECTION DEVICE

(75) Inventors: Joseph H. Jackson, III, El Granada, CA (US); Dean G. Hafeman, Hillsborough, CA (US); Todd E. French, Mountain View, CA (US)

(73) Assignee: Molecular Devices Corporation, Sunnyvale, CA (US)

( * ) Notice: Subject to any disclaimer, the term of this patent is extended or adjusted under 35 U.S.C. 154(b) by 192 days.

(21) Appl. No.: 10/003,030

(22) Filed: Oct. 29, 2001

(65) Prior Publication Data

US 2002/0109100 A1 Aug. 15, 2002

Related U.S. Application Data (60) Provisional application No. 60/244,012, filed on Oct. 27, 2000.

(51) Int. Cl.[7] .................................................. G01J 1/58
(52) U.S. Cl. ................. 250/458.1; 356/213; 356/445; 356/246; 356/72; 435/6; 435/173.9
(58) Field of Search ........................ 250/458.1; 356/213, 356/445, 246, 72; 435/6, 173.9

(56) References Cited

U.S. PATENT DOCUMENTS

| | | |
|---|---|---|
| 3,975,098 A | 8/1976 | West |
| 4,460,274 A | 7/1984 | Schumann et al. |
| 4,537,861 A | 8/1985 | Elings et al. |
| RE32,598 E | 2/1988 | White |
| 5,355,215 A | 10/1994 | Schroeder et al. |
| 5,477,332 A * | 12/1995 | Stone et al. ................. 356/613 |
| 5,828,452 A | 10/1998 | Gillispie et al. |
| 5,938,617 A * | 8/1999 | Vo-Dinh ...................... 600/476 |
| 5,973,842 A * | 10/1999 | Spangenberg ............... 359/619 |
| 5,978,095 A * | 11/1999 | Tanaami ...................... 356/445 |
| 6,011,626 A * | 1/2000 | Hielscher et al. ........... 356/367 |
| 6,097,025 A | 8/2000 | Modlin et al. |
| 6,759,662 B1 * | 7/2004 | Li ............................ 250/458.1 |
| 2002/0176801 A1 * | 11/2002 | Giebeler et al. .......... 422/82.05 |

FOREIGN PATENT DOCUMENTS

| | | |
|---|---|---|
| WO | WO 00/06990 | 2/2000 |
| WO | WO 00/06991 | 2/2000 |
| WO | WO 00/50877 | 8/2000 |
| WO | WO 00/66269 | 11/2000 |
| WO | WO 01/04608 | 1/2001 |

* cited by examiner

*Primary Examiner*—David Porta
*Assistant Examiner*—Christine Sung
(74) *Attorney, Agent, or Firm*—Dorsey & Whitney LLP (57) ABSTRACT

Apparatus and methods for optical illumination and/or detection with improved flexibility and/or read speed. The apparatus and methods may include mechanisms for selecting and switching between multiple excitation wavelengths and/or simultaneously reading from a plurality of sample sites. The apparatus and methods may be used with microplates, PCR plates, cell culture plates, biochips, chromatography plates, microscope slides, and other substrates for high-throughput screening, genomics, SNPs analysis, pharmaceutical research and development, life sciences research, and other applications.

18 Claims, 5 Drawing Sheets

LIGHT DETECTION DEVICE

CROSS-REFERENCE

This application is based upon and claims the benefit under 35 U.S.C. § 119 and all applicable foreign and international law of the following U.S. provisional patent application, which is hereby incorporated by reference in its entirety for all purposes: Ser. No. 60/244,012, filed Oct. 27, 2000.

This application hereby incorporates by reference in their entirety for all purposes the following U.S. Pat. No. 5,355, 215, issued Oct. 11, 1994; and No. 6,097,025, issued Aug. 1, 2000.

This application hereby incorporates by reference in their entirety for all purposes the following U.S. patent application Ser. No. 09/337,623, filed Jun. 21, 1999; Ser. No. 09/349,733, filed Jul. 8, 1999; Ser. No. 09/478,819, filed Jan. 5, 2000; Ser. No. 09/596,444, filed Jun. 19, 2000; Ser. No. 09/710,061, filed Nov. 10, 2000; Ser. No. 09/722,247, filed Nov. 24, 2000; Ser. No. 09/759,711, filed Jan. 12, 2001; Ser. No. 09/765,869, filed Jan. 19, 2001; Ser. No. 09/765,874, filed Jan. 19, 2001; Ser. No. 09/766,131, filed Jan. 19, 2001; Ser. No. 09/767,434, filed Jan. 22, 2001; Ser. No. 09/767, 579, filed Jan. 22, 2001; Ser. No. 09/767,583, filed Jan. 22, 2001; Ser. No. 09/768,661, filed Jan. 23, 2001; Ser. No. 09/768,765, filed Jan. 23, 2001; Ser. No. 09/770,720, filed Jan. 25, 2001; Ser. No. 09/770,724, filed Jan. 25, 2001; Ser. No. 09/777,343, filed Feb. 5, 2001; Ser. No. 09/813,107, filed Mar. 19, 2001; Ser. No. 09/815,932, filed Mar. 23, 2001; and Ser. No. 09/836,575, filed Apr. 16, 2001; and Ser. No. 09/934,348, filed Aug. 20, 2001; and Ser. No. 09/957, 116, filed Sep. 19, 2001.

This application hereby incorporates by reference in their entirety for all purposes the following U.S. Provisional Patent Applications: Ser. No. 60/223,642, filed Aug. 8, 2000; Ser. No. 60/244,012, filed Oct. 27, 2000; Ser. No. 60/267, 639, filed Feb. 10, 2001; Ser. No. 60/287,697, filed Apr. 30, 2001; Ser. No. 60/309,800, filed Aug. 2, 2001; and Ser. No. 60/316,704, filed Aug. 31, 2001.

This application also hereby incorporates by reference in their entirety for all purposes the following publications: Joseph R. Lakowicz, *Principles of Fluorescence Spectroscopy* ($2^{nd}$ ed. 1999); and Bob Sinclair, *Everything's Great When It Sits on a Chip: A Bright Future for DNA Arrays*, 13 THE SCIENTIST, May 24, 1999, at 18.

FIELD OF THE INVENTION

The invention relates to optical detection. More particularly, the invention relates to apparatus and methods for optical illumination and/or detection with improved flexibility and/or read speed.

BACKGROUND OF THE INVENTION

Spectroscopy involves the study of matter using electromagnetic radiation. Spectroscopic measurements can be separated into three broad categories: absorbance, scattering/reflectance, and emission. Absorbance assays involve relating the amount of incident light that is absorbed by a sample to the type and number of molecules in the sample. Absorbance assays are a powerful method for determining the presence and concentration of an analyte in a sample. Most commonly, absorbance is measured indirectly by studying the portion of incident light that emerges from the sample. Scattering assays are similar to absorbance in that the measurement is based on the amount of incident light that emerges or is transmitted from the sample. However, in the case of scattering, the signal increases with the number of interactions, whereas, in the case of absorbance, the signal is inversely proportional to the interactions. Emission assays look at electromagnetic emissions from a sample other than the incident light. In each case, the measurements may be broad spectrum or frequency specific depending on the particular assay. Most commonly, emission assays involve the measurement of luminescence. The techniques of absorbance, scattering/reflectance, and luminescence are described in detail in the following patent applications, which are hereby incorporated by reference in their entirety for all purposes: WIPO Publication No. WO 00/06991, published Feb. 10, 2000; and corresponding U.S. patent application Ser. No. 09/765,869, filed Jan. 19, 2001.

Luminescence is a preferred assay technique due to its specificity and sensitivity, among others. Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, which includes fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence assays are assays that use luminescence emissions from luminescent analytes to study the properties and environment of the analyte, as well as binding reactions and enzymatic activities involving the analyte, among others. In these assays, the analyte itself may be the focus of the assay, or the analyte may simply act as a reporter that provides information about another material or target substance that is the true focus of the assay. Recently, luminescence assays have been used in high-throughput procedures to screen pharmaceutical drug candidate libraries for drug activity and to identify single-nucleotide polymorphisms (SNPs).

Luminescence assays may involve detection and interpretation of one or more properties of the luminescence or associated luminescence process. These properties may include intensity, excitation and/or emission spectrum, polarization, lifetime, and energy transfer, among others. These properties also may include time-independent (steady-state) and/or time-dependent (time-resolved) properties of the luminescence. Representative luminescence assays include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and bioluminescence resonance energy transfer (BRET), among others.

Luminescence assays have been conducted using various light sources, including arc lamps and lasers. Unfortunately, these light sources suffer from a number of shortcomings. The gas used in arc lamps typically is under high pressure, so that explosion is always a danger, and the associated power supplies may produce transients that can damage other electronic components of the system. The lifetime of arc lamps may be short, so that the lamps must be changed frequently. Moreover, typical arc lamps (including flash arc lamps) suffer from intensity instability, with short-term noise of several percent, which is much worse than good lasers such as laser diodes and diode pumped solid-state lasers, with short-term noise of typically less than 0.5%. In addition, lamps have a slow and steady long-term decay of intensity, whereas lasers normally exhibit a constant intensity up until catastrophic failure. The spectral output of some arc lamps and most lasers is very limited, so that desired excitation wavelengths may not be available. For example, two commonly used light sources, the mercury arc lamp and the argon-ion laser, produce significant visible light only at two wavelengths below about 550 nm. Moreover, the procedure for switching or tuning between these wavelengths can be so cumbersome and impractical that some experimentalists have resorted to the expensive alternative of incorporating multiple lasers into their instrumental setups. Significantly, an ability to use and switch between various excitation wavelengths would permit use of a wider variety of dyes, which in turn would facilitate the development of new luminescence assays, including new high-throughput cell-based luminescence assays.

Luminescence assays also have been conducted using various detection schemes. These schemes may require alignment of a sample and portions of an optical relay structure (such as an optics head) for directing light to and from the sample. This alignment typically is accomplished by physically moving the sample relative to the optical relay structure and/or by physically moving the optical relay structure relative to the sample. This movement may be followed by a waiting period before measurement to allow vibrations to subside. Time spent during alignment and subsequent waiting periods is downtime because it is time during which data cannot be collected from the sample. This downtime is especially significant in high-throughput screening, where tens or hundreds of thousands of samples must be aligned with an optical relay structure to conduct a particular study.

In principle, reading simultaneously from a plurality of samples or from a larger area of a single sample can reduce the number of alignment steps and thus the amount of downtime in these assays. Indeed, instrumentation has been developed that directs light from an arc lamp or from a continuous wave laser tuned to a single fixed wave length to multiple wells of a microplate using a mechanical (e.g., rotating polygon or galvanometric) scanner and/or a wide-field illuminator. However, reading with the scanner is slow, because samples are analyzed well by well, and reading with the wide-field imager reduces intensities, because excitation light is distributed to areas between or outside the samples. Reduced intensities may decrease signal-to-noise ratios, decreasing reliability, especially with less intense nonlaser light sources. Prior art instrument systems also may be limited because it may be difficult to change the emission filter to correspond to a change in excitation wavelength. This is especially true with simultaneous reading because filters for simultaneous reading may need to be quite large to filter emission light passing from large-area samples, such as microplates, to large-area imaging devices, such as charge-coupled devices (CCDs), charge injection device (CID) arrays, videcon tubes, photomultiplier tube arrays, position sensitive photomultiplier tubes, and the like. Significantly, it is desirable to increase the number of measurements made in a given time period. Increased data collection rates together with faster analysis would give more specific and quantitative information regarding the speed and strength of cellular responses to potential drug candidates.

SUMMARY OF THE INVENTION

The invention provides apparatus and methods for optical detection with improved flexibility and/or read speed, including mechanisms for selecting and switching between multiple excitation wavelengths and/or simultaneously reading from a plurality of sample sites.

BRIEF DESCRIPTION OF THE DRAWINGS

FIG. 6 shows calcium flux response in the presence and absence of added carbachol as determined by an apparatus of the invention, as described in Example 6.

DETAILED DESCRIPTION

The invention provides apparatus and methods for optical illumination and/or detection with improved flexibility and/or read speed.

The apparatus and methods may include mechanisms for selecting and switching between multiple excitation wavelengths, particularly from a continuously variable band of excitation wavelengths. This ability to select and switch may permit use of a wider variety of dyes and may facilitate the development of new dyes and new luminescence assays. This ability may involve combining a laser or other monochromatic light source with a wavelength converter mechanism for converting monochromatic light into light of at least two or more different wavelengths. The step of converting light may be automatic, for example, switchable by software, so that associated assays may be automated. Preferred implementations may include the combination of a pulsed YAG laser with an optical parametric oscillator.

The apparatus and methods also may include mechanisms for simultaneously reading from a plurality of sample sites, particularly without significantly illuminating regions between the sample sites. This ability may reduce required movements of the sample substrate and/or optics, potentially increasing data collection rates by decreasing downtime. This ability may involve using an optical pattern generator that converts input light into output light having a preselected intensity pattern corresponding to a plurality of sample sites representing some or all of the sample sites in a particular sample holder, such as a microplate. Preferred implementations may include a binary diffractive chip and/or a refractive or reflective array, such as a lens or mirror array or a suitable beamsplitter.

The following sections describe further aspects of the invention, including (I) an overview of the apparatus, (II) applications, and (III) examples.

I. Overview of Apparatus

Figure 1:
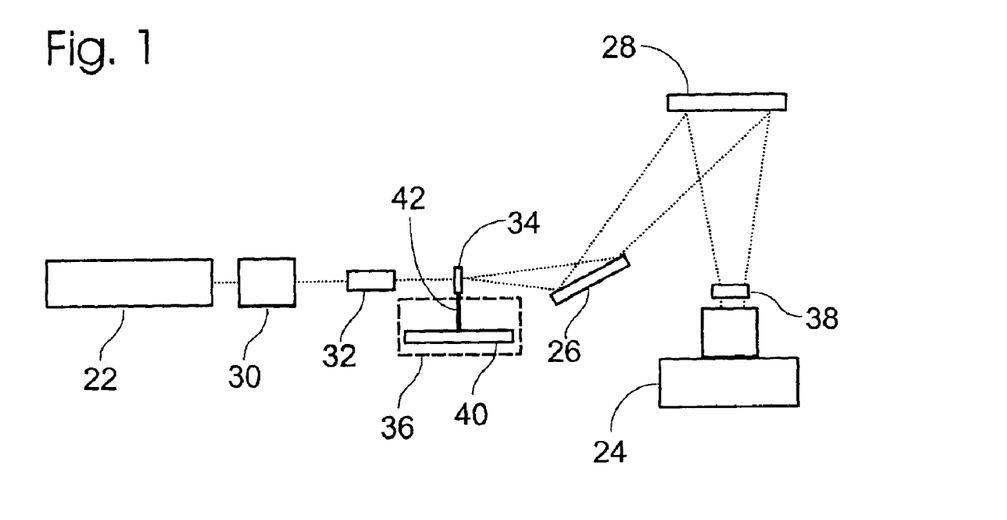
FIG. 1 is a schematic side view of a light detection device, constructed in accordance with aspects of the invention, as described in Example 1. The device is capable of optical illumination and/or detection.

FIG. 1 is a schematic view of a light detection device 20 constructed in accordance with aspects of the invention. The apparatus generally includes a light source 22, a detector 24, and an optical relay structure 26 configured to direct light from the light source to a sample holder 28 and/or from the sample holder to the detector. The apparatus also may include a wavelength converter 30, a collimator 32, an optical pattern generator 34, a compensator 36, and/or an emission spectral filter 38, among others. These components are described below, generally in the order in which they appear in the optical path.

A. Light Source

The light source (22) generally comprises any mechanism capable of producing light suitable for use in an optical assay, such as photoluminescence, scattering, and/or absorbance assays, among others. Suitable light sources include lasers, arc lamps, incandescent lamps, fluorescent lamps, electroluminescent devices, laser diodes, and light-emitting diodes (LEDs), among others. The light source may be capable of use in one or more illumination modes, including continuous and/or time-varying modes, among others, such as a pulsed laser. The light source may be capable of producing coherent and/or incoherent, and polarized and/or unpolarized, light. Preferred light sources include a Q-switched YAG laser, a Nd:glass laser, a Nd:V04 laser, a Nd:YAG laser, a nitrogen laser, a Q-switched argon laser, a Ti:sapphire laser, and a fiber (Er, Yt, etc.) laser and, more generally, any other laser or monochromatic light source.

B. Wavelength Converter

The wavelength converter (30) generally comprises any device or other mechanism capable of converting light of one wavelength into light of another wavelength, particularly light of a longer wavelength. The mechanism may involve converting light of a single wavelength into light of two or more wavelengths, for example, by conversion of an input photon into a signal photon and an idler photon, where the energy of the input photon is equal to the sum of the energies of the signal and idler photons. A preferred wavelength converter is an optical parametric oscillator (OPO), particularly in combination with a pulsed YAG laser. The OPO includes a crystal that exhibits an angle-dependent birefringence, such that the crystal may be used to convert an incoming photon into two lower-energy longer-wavelength photons having energies and wavelengths determined by the angle between the incident light and the crystal lattice. These energies and wavelengths may be at least substantially continuously variable, so that the wavelength of the second photon may vary by two percent, five percent, ten percent, twenty percent, or any suitable percent from the wavelength of the first photon. In particular, the YAG laser may include one or more harmonic generators (crystals housed within the YAG box) that produce $2^{nd}$ (532 nm) and $3^{rd}$ (355 nm) harmonics of the 1064-nm fundamental wavelength of the YAG laser. In a preferred configuration, the $3^{rd}$ harmonic is used to excite the OPO. Specifically, the $2^{nd}$-harmonic generator is used to produce the 532-nm $2^{nd}$ harmonic from the 1064-nm fundamental, the $3^{rd}$-harmonic generator is used to produce the 355-nm $3^{rd}$-harmonic from the $2^{nd}$ harmonic, and the $3^{rd}$-harmonic is directed into the OPO. In summary, the output wavelength may be selected, manually or automatically, for example, using a mechanical adjustment, creating a source of continuously tunable coherent radiation.

Suitable YAG/OPO combinations are available from Continuum Laser (Santa Clara, Calif.). These combinations may deliver light in pulses of about 1–50 nanoseconds in duration at repetition rates of about 1–20 Hz over wavelengths of about 400–2500 nanometers. Preferred combinations, as they become available, would deliver light in any arbitrary pulse width, at continuous wave (CW) or quasi-continuous-wave repetition rates, over wavelengths of about 150–2500 nanometers. Combinations with a slow pulse width may be used with a beamsplitter, if desired. The hardware for selecting and/or adjusting wavelength may be computer controlled.

C. Collimator

The collimator (32) generally comprises any mechanism capable of converting input light (particularly diverging input light) into a substantially parallel collimated light beam. Suitable collimators include adjustable-focus telescopic beam expanders, for example, positioned to receive and re-collimate laser light output by an OPO. A collimator is especially desirable immediately downstream from an OPO because an OPO may introduce significant divergence into a laser beam and thereby interfere with the operation of downstream optics, such as an optical pattern generator. Alternatively, a collimator may be used without an optical pattern generator, acting as a spot light rather than a scanner, and giving up the benefit of illuminating only the sample regions.

D. Optical Pattern Generator

The optical pattern generator (34) generally comprises any mechanism capable of converting input light into output light having a preselected intensity pattern. This pattern may be created using diffraction, refraction, reflection, and/or other mechanisms, or a combination thereof. The optical pattern generator preferably comprises a diffractive (e.g., binary) optical element containing a glass, plastic, and/or fused silica chip designed and patterned by holography, photolithography, scribing, molding, and/or other methods to create a predefined illumination pattern from incident light. The optical pattern generator alternatively, or in addition, may comprise a refractive or reflective optical element, such as a lens or mirror array or beamsplitter, among others.

The optical pattern generator may be used to generate any desired pattern of light, including one-dimensional or two-dimensional patterns (or arrays) and periodic or aperiodic patterns. For example, a diffractive chip or similar optical pattern generator may be used to create any regularly shaped beamlet array of any dimension, with up to 100,000 or more beamlets, and up to a square meter or more in size. Here, a diffractive chip from Edmund Scientific was used to produce an 8×8 array of beamlets (as described in Example 1). Typically, the pattern will be selected based on application. For example, in microplate applications, the desired pattern may be an array of substantially equally spaced substantially equally intense spots positioned to correspond to the spacing of some or all of the wells of a microplate. (A high-throughput instrument may be successful without illuminating all sample wells simultaneously, especially if the instrument has a strategy for efficiently addressing sets of wells.) Thus, an 8-beamlet array (8×1 or 4×2) or a 16-beamlet array (8×2 or 4×4) may be produced to correspond to some of the wells in a 96, 384, or 1536-well microplate, among others. Similarly, a 96-beamlet array (8×12) or a 384-beamlet array (16×24) or a 1536 beamlet array (32×48) may be produced to correspond to all of the wells in a 96, 384, or 1536-well microplate, among others. In these examples, the arrays could be positioned such that the corresponding spots illuminate all wells within a particular (e.g., rectangular) region, for example, with the spots separated by 9 mm, 4.5 mm, and 2.25 mm when projected or focused onto a 96, 384, and 1536-well microplate, respectively. In this approach, all wells in a plate may be addressed by translating the illuminated region the width of the illuminated region, one or more times, among other mechanisms. Alternatively, the arrays could be positioned such that the corresponding spots form a sparse array covering a fraction of the wells over a larger region of the plate, for example, with the spots illuminating either other or every fourth well, among others. In this approach, all wells in a plate may be addressed by translating the illumination pattern one well spacing, one or more times, among other mechanisms.

The desired pattern ideally will provide uniform light intensity across each well and across the entire plate, although this is not required for the technique to succeed. (For example, in some applications, the desired pattern may correspond to two or more beamlets per sample site, rather than just one.) Generally, it is easier to produce uniform illumination across individual samples than across the entire illumination pattern, particularly with very large area arrays. However, uniform illumination across the entire pattern is unnecessary for many assays, particularly assays such as kinetic and cellular assays that involve reading the samples (i.e., taking a measurement) before (prereading) and after (reading) initiation of the kinetic or cellular assay, since the pre-initiation measurement may act as a reference or calibration for the post-initiation measurement. Initiation of a kinetic assay may be accomplished by addition of a key assay component (e.g., via fluid transfer), electrical stimulation (e.g., via field-stimulating cells for electrically responsive assays or electrochemiluminescent assays), and/or photoactivation of key assay components and other similar means. Suitable field-stimulating cells are described in U.S. patent application Ser. No. 09/934,348, filed Aug. 20, 2001, which is hereby incorporated by reference in its entirety for all purposes. The apparatus and methods of the invention enable photoactivation by the tunable light source that quickly can be configured to send one burst of energy (e.g., a pulse) to initiate the assay, followed by the monitoring wavelength used to induce luminescence.

The optical pattern generator also may employ nondiffractive optics. For example, the generator could employ a lens array that focuses a large collimated beam. The collimated beam from the collimator (e.g., telescope) would be beam expanded and directed into a lenslet array that would focus the separated light onto multiple sample sites, without using a diffractive optic. Similarly, the generator could employ solid optics such as a beam splitter.

The pattern generated by the optical pattern generator may be projected into the examination site to illuminate a sample holder at any suitable angle, including right angles and/or oblique angles, as described below. Right angle illumination, as used in epi and trans illumination, is straightforward. However, oblique illumination creates an additional challenge, in that a uniform array spacing will not project onto the sample holder as a uniform array. Instead, the optical pattern generator must be built to compensate for the oblique illumination. The spacing of the illumination pattern at the sample holder should match the sample spacing. Thus, the pattern generator should have a beamlet spacing that varies across the element, for example, in FIG. 1, becoming more compressed going from left to right on the microplate. However, if the array is sufficiently small, it may be useable as is, with the distortion in spacing causing little variance in illumination.

E. Compensator

The compensator (36) generally comprises any mechanism capable of adjusting the relative positions and/or orientations of the optical pattern generator and sample to compensate for wavelength-dependent differences in the pattern produced by the optical pattern generator. A compensator is especially desirable in systems that include a wavelength-sensitive optical pattern generator, such as a diffractive optic, particularly if the optic is used at wavelengths other than its design wavelength.

Suitable compensators include translation and/or rotation stages, among others. A preferred compensator includes a linear translation stage 40 and an associated mount 42 configured to hold the optical pattern generator. The preferred compensator may be configured to move a diffractive optic or other pattern generator along the line of an incoming laser beam, nearer or farther from the sample. For example, to achieve the same array spacing with the Edmund Scientific optic described above, the proper distance for 488-nm light was 28.9 inches, whereas the proper distance for 632-nm light was 18.65 inches. The compensator may be motorized and computer controlled to compensate automatically for changes in selected wavelength, for example, by using a lookup table and/or a sensor feedback system to position and/or orient components.

F. Optical Relay Structure

The optical relay structure (26) generally comprises any mechanism capable of directing light from a light source toward a sample (or examination site) and/or from a sample (or examination site) toward a detector. Suitable optical relay structures may include mirrors, lenses, and/or fiber optics, among others. Preferred optical relay structures include apochromatic elements, such as reflective optics elements. For example, the system of FIG. 1 includes a fold mirror positioned operatively between the optical pattern generator and a sample holder and configured to direct light from the optical pattern generator onto samples positioned in the sample holder.

The optical relay structure may be selected to allow any of a variety of combinations of top and/or bottom illumination and/or detection of a sample holder, including the following specific combinations: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and is preferred for absorbance assays.

Alternatively, or in addition, the optical relay structure may be selected such that illumination and/or detection occur at oblique angles. For example, illumination light may impinge on the bottom of a sample holder at an acute angle (e.g., about 45 degrees) relative to detection. In comparison with a straight-on epi system (light source and detector directed at about 90 degrees to sample holder) or a straight-through trans system (light source directed through sample holder directly at detector), an oblique system may reduce the amount of excitation light reaching the detector. An oblique system also may be used for unique kinds of illumination, such as total internal reflection.

Suitable optical relay structures for top/bottom and/or oblique illumination and/or detection are described in U.S. Pat. No. 5,355,215, issued Oct. 11, 1994; U.S. Pat. No. 6,097,025, issued Aug. 1, 2000; U.S. patent application Ser. No. 09/337,623, filed Aug. 16, 1999; and U.S. Provisional Patent Application Ser. No. 60/267,639, filed Feb. 10, 2000, each of which is hereby incorporated by reference in its entirety for all purposes.

G. Sample Holder

The sample holder (28) generally comprises any mechanism capable of supporting a sample and particularly a plurality of samples at a corresponding plurality of sample sites for analysis. Suitable sample holders include microplates, PCR plates, cell culture plates, biochips, hybridization chambers, chromatography plates, and microscope slides, among others, where microplate wells and biochip array sites may comprise assay sites. Preferred microplates are described in the following U.S. patent applications, each of which is hereby incorporated by reference in its entirety for all purposes: Ser. No. 08/840,553, filed Apr. 14, 1997; Ser. No. 09/156,318, filed Sep. 18, 1998; and Ser. No. 09/478,819, filed Jan. 5, 2000. These microplates (and/or cell culture plates) may include 6, 12, 24, 48, 96, 384, 864, 1536, 3456, 9600, and/or other numbers of wells. These microplates also may include wells having elevated bottoms, small ($\leqq 50$ $\mu$L) volumes, and/or frusto-conical shapes capable of matching a sensed volume. A "standard" microplate includes 96 cylindrical sample wells disposed in a 8×12 rectangular array on 9 millimeter centers. Preferred PCR plates may include the same (or similar) footprints, well spacings, and/or well shapes as the preferred microplates, while possessing stiffness adequate for automated handling and thermal stability adequate for PCR. Preferred biochips are described in Bob Sinclair, *Everything's Great When It Sits on a Chip: A Bright Future for DNA Arrays*, 13 THE SCIENTIST, May 24, 1999, at 18. Preferred hybridization chambers are described in U.S. patent application Ser. No. 09/767,434, filed Jan. 22, 2001, which is hereby incorporated by reference in its entirety for all purposes.

H. Emission Spectral Filter

The emission spectral filter (38) generally comprises any mechanism capable of selecting the wavelength composition (or spectrum) of light admitted to the detector. Suitable emission spectral filters include interference filters, liquid crystal tunable filters, acousto-optic tunable filters, gratings, monochromators, and/or prisms, among others. One or more filters having suitable spectral characteristics (e.g., cutoff wavelength) may be housed in a filter selector such as a filter wheel or filter slider so that the wavelength composition of the emission light admitted to the detector may be changed by rotating or sliding or otherwise placing a preselected filter into the optical path. Any of the filters or filter selectors may be placed under computer control to automate filter passband selection in coordination with excitation wavelength selection.

Emission spectral filters may be used to transmit emission light and block excitation light in photoluminescence applications. Specifically, emission spectral filters with appropriate cutoff wavelengths can separate emitted or transmitted light from incident or illumination light due to differences in wavelength. For example, in conventional photoluminescence assays, the detected (emission) light is of longer wavelength than the corresponding illumination (excitation) light. In contrast, in multiphoton photoluminescence assays (and in anti-Stokes Raman scattering), the detected light is of shorter wavelength than the corresponding illumination light. In the absence of an emission filter, stray excitation light created, for example, by scattering and/or reflection may be detected and misidentified as photoluminescence, decreasing the signal-to-background ratio. Emission spectral filters for photoluminescence applications typically have wavelength cutoffs between about 200 and about 2000 nanometers.

I. Detector

The detector (24) generally comprises any mechanism capable of detecting light transmitted from a sample and converting the detected light to a representative signal. Suitable detectors include charge-coupled devices (CCDs), intensified charge-coupled devices (ICCDs), charge injection device (CID) arrays, videcon tubes, photomultiplier tubes (PMTs), photomultiplier tube arrays, position sensitive photomultiplier tubes, photodiodes, and avalanche photodiodes, among others. The detector may be capable of use in one or more detection modes, including (a) imaging and point-reading modes, (b) discrete (e.g., photon-counting) and analog (e.g., current-integration) modes, and (c) steady-state and time-resolved modes, among others. The detector may be capable of automatically scaling the detection range and/or automatically selecting and switching between detection modes to improve detection accuracy, as described in U.S. patent application Ser. No. 09/643,221, filed Aug. 18, 2000, which is hereby incorporated by reference in its entirety for all purposes.

Preferred detectors include CCDs and ICCDs, the latter being especially suitable for the detection of low-intensity light generated using pulsed lasers. The image-intensifier screen in front of the CCD chip in the ICCD may be activated selectively during desired time windows by supplying a voltage during the time windows. These windows may be of any suitable duration, including very short duration, e.g., a nanosecond or shorter, or of long duration, e.g., a minute or longer. Thus, the image intensifier may be used as a super-fast shutter capable of operating on nanosecond time scales, so that time-resolved fluorescence may be monitored over a very wide dynamic range of times. By supplying the voltage for a series of incrementally delayed time windows after excitation light pulses, the emission intensity as a function of delay time may be measured, thereby supplying a measure of the photoluminescence (e.g., fluorescence or phosphorescence) lifetime of the luminescence signals. The frequency domain equivalents also may be applied. In this case, the image intensifier gain and the illumination intensity are modulated at high frequency. The two signals heterodyne (homodyne) at the CCD (no high frequencies pass), and the phase and modulation can be determined. Further advantages and example usages of such time-resolved methods are described below.

Preferred detectors also include PMTs, in particular fast PMTs capable of monitoring emission over time scales between about 0.1 nanosecond and about 1 second. PMTs may be used singly or in arrays of two or more PMTs configured to detect light from a corresponding array of samples. PMTs may be especially useful in time-resolved assays, for example, to determine photoluminescence lifetime and/or time-resolved polarization, among others, using pulses of excitation light.

J. Reference Monitor

The reference monitor generally comprises any mechanism capable of correcting for variations (e.g., fluctuations and/or inhomogeneities) in light produced by the light source and/or other optical elements. The reference monitor optionally may sample the intensity of the input beam (e.g., with each pulse) to provide a baseline for correcting measured photoluminescence levels (e.g., at different positions within a pattern). For example, the reference monitor may be used to compensate for input beam variations due to pulse-to-pulse variations in output energy from the light source by reporting detected intensities as a ratio of the photoluminescence intensity measured by the detector to the excitation light intensity measured for the same time by the reference monitor. The reference monitor also may be used to perform additional functions, such as pausing device operation and/or alerting an operator if a light source fails or if light source intensities fall outside a preselected range.

The reference monitor may divert and sample light using any suitable mechanism. For example, depending on the type of optical pattern generator, the intensity of the light beam may be sampled using a beamsplitter device placed before and/or after the optical pattern generator, where the reference monitor receives light from the beamsplitter. Alternatively, or in addition, the reference monitor could be placed at one or more sites in the array of beamlets produced by the diffractive optic. For example, with a diffractive element, the zeroth-order beam may be diverted to the reference monitor, particularly with large beamlet arrays, in which it is difficult to remove the zeroth-order beam. Moreover, a selected well of a microplate containing a fluorescent material could be used as a reference for normalization of data with respect to light source intensity. Generally, the reference monitor may detect the diverted and sampled light using any detector capable of detecting the light and converting it to a signal suitable for use in correcting the sample signal(s).

K. Miscellaneous Optical Elements

The apparatus also may include miscellaneous optical elements capable of performing additional and/or duplicative optical functions, such as "intensity filters" for reducing the intensity of light, "polarizers" for altering the polarization of light, and "confocal optics elements" for reducing out-of-focus light. Suitable miscellaneous optical elements and their implementation are described in U.S. Pat. No. 5,355,215, issued Oct. 11, 1994; U.S. Pat. No. 6,097,025, issued Aug. 1, 2000; U.S. patent application Ser. No. 09/337,623, filed Aug. 16, 1999; and U.S. Provisional Patent Application Ser. No. 60/267,639, filed Feb. 10, 2000, each of which is hereby incorporated by reference in its entirety for all purposes.

The relative positions of spectral, intensity, polarization, and other optical elements generally may be varied without affecting the operation of the apparatus. In addition, if there is more than one optical path, for example, to permit top and bottom illumination and/or detection, filters may be used independently in each path. The optimal order, positions, and combinations of filters for a particular experiment generally will depend on the apparatus, the assay mode, and the sample, among other factors.

L. Additional Elements

The apparatus also may include additional components and/or systems, including a fluidics module, a sample handling module, an analysis module, and/or other modules. Suitable components and systems are described in the patents and patent applications listed above under Cross-References and incorporated herein by reference, particularly U.S. Pat. No. 5,355,215, issued Oct. 11, 1994; U.S. patent application Ser. No. 09/777,343, filed Feb. 5, 2001; and U.S. Provisional Patent Application Ser. No. 60/267,639, filed Feb. 10, 2001, among others. The fluidics module may be used to allow simultaneous and/or sequential fluid dispensing and sample reading. For example, a reagent may be dispensed at two or more sample sites using a multichannel dispense or pipettor head, and then light such as luminescence may be detected from those sample sites by illuminating them with a pattern created by an optical pattern generator. The sample handling module may include a stage and/or other suitable mechanisms for supporting and/or transporting sample holders to an from an examination site. Suitable sample handling modules are described in U.S. patent application Ser. No. 09/777,343, filed Feb. 5, 2001, which is hereby incorporated by reference in its entirety for all purposes.

II. Applications

The apparatus of the invention generally is adapted to detect the occurrence of, or changes in, a luminescence signal from a sample such as a photoactive analyte due to excitation by the light source via the wavelength converter and/or the optical pattern generator. The apparatus typically detects a change in sample luminescence, such as a change in the intensity, excitation and/or emission spectrum, polarization, and/or lifetime of the sample luminescence, or a combination thereof. The apparatus generally may be used in any suitable application, including high-throughput screening, genomics, SNPs analysis, pharmaceutical research and development, life sciences research, and/or other applications.

The detectable luminescence response may simply be detected, or it may be quantified. Where it is quantified, the intensity, wavelength, polarization, lifetime, and/or other spectral property of the luminescence response may be compared to a calibration standard. This standard may be the result of a calibration curve, a calculation of an expected response, or a luminescent reference material such as a luminescently labeled microparticle. The standard may be control samples present in selected wells of a multiwell microplate that also contains one or more samples.

The sample typically is a solution, cell, tissue, or other system containing one or more biomolecules that are biological in origin and/or that have been synthetically prepared. The sample optionally is or is derived from a biological sample that is prepared from a blood sample, urine sample, a swipe, a smear, or other physiological sampling method. Alternatively, the sample optionally is or is derived from an environmental sample, such as an air sample, a water sample, or a soil sample. The sample typically is aqueous, but may contain biologically compatible organic solvents, buffering agents, inorganic salts, or other components known in the art for assay solutions. Suitable samples (or compositions) include compounds, mixtures, surfaces, solutions, emulsions, suspensions, cell cultures, fermentation cultures, cells, suspended cells, adherent cells, tissues, secretions, and/or derivatives and/or extracts thereof. Depending on the assay, the term "sample" may refer to the contents of a single sample site (e.g., microplate well) or of two or more sample sites.

The detectable luminescence response may be used to determine the presence, absence, concentration, activity, and/or physical properties (including interactions) of a photoactive analyte in the sample. The apparatus may be used to detect a change in one or more samples, for example, due to a change in sample temperature and/or the addition of one or more reagents to the sample. In the latter case, the reagent may be a chemical reagent, or it may have a known or suspected biological activity or type of interaction with the sample. The apparatus also may be used to detect or quantify one or more aspects of biological activity in a sample.

The apparatus and methods described above may provide one or more advantages over prior devices and techniques, including, without limitation, those described below.

The pulsed YAG/OPO combination is capable of providing multiple wavelengths of excitation light, which may increase the number and type of assays that may be developed and performed by the apparatus and methods described here. These multiple wavelengths are available in a continuous band from about 400 to 700 nm, from about 700 to 1000 nm, and from about 1000 nm to 2500 nm. Moreover, these multiple wavelengths may be selected easily and automatically simply by changing parameters of the YAG/OPO.

The diffractive optical element may divide the single incoming laser beam into 96 or 384 or even more separate beamlets, each capable of addressing a single sample site (for example, discrete wells of a microplate). Because this method may address all wells simultaneously, it may reduce or eliminate the need for a mechanical scanner. Scanning a pulsed laser from well to well at a rate of 10 Hz may be a prohibitively slow method for acquiring data from microplates having 96, or more, wells.

The short (5–8 ns) laser pulses created by the YAG/OPO system may provide several advantages. First, the short pulses allow the laser to be used to perform time-resolved fluorescence assays, in addition to the more usual (e.g., steady-state) modes of operation and analysis. Second, the combination of short pulses and simultaneous illumination from the diffractive optical element may greatly increase the rate of data collection from the microplate. Specifically, no time need be lost during the assay from scanning the laser to different wells, and the energy required for efficient excitation is delivered in a very short period of time. In addition, the detection time window (e.g., camera shutter open time) can be shortened dramatically with a commensurate reduction in the amount of background light (i.e., noise) collected by the detector.

If the beam is not scanned across the interstitial spaces separating the wells of the microplate, no light energy is wasted illuminating areas that do not contain sample and that therefore do not have information value. Also, if the beam is not scanned across the interstitial spaces, background levels of illumination during exposure are reduced, decreasing noise and increasing sensitivity.

If a diffractive optical element is used as the optical pattern generator to send light from each part of the incoming beam to each sample site (e.g., well of a microplate), the energy distribution of the output beamlet will be homogenized, and potential spatial variations in the energy intensity profile of the input beam will not be reflected in varying levels of excitation from well to well over time. It still is possible to have variations of total beam energy shot-to-shot, but these variations can be measured with the reference monitor and easily compensated for in the data reduction step.

If an ICCD is used as a detector, as described above, or a fast shutter (preferably an electronic shutter, such as a gated cathode, liquid crystal, or equivalent shutter, but also a fast mechanical shutter, such as a fast solenoid, very small-aperture tuning fork, or small aperture synchronized chopper wheel) is added in the detection path, the short (picosecond-millisecond) gating then available will enable a variety of additional analytical techniques to be employed in a high-throughput mode. These include, but are not limited to, homogeneous time-resolved fluorescence (HTRF), time-resolved fluorescence resonance energy transfer (TR-FRET), time-domain or frequency-domain luminescence lifetime based assays, and/or lifetime-resolved measurements, such as FLARe, among others. Suitable apparatus and methods for time-resolved assays are described in the following U.S. patent applications, which are hereby incorporated by reference in their entirety for all purposes: Ser. No. 09/626,208, filed Jul. 26, 2000; Ser. No. 09/722,247, filed Nov. 24, 2000; Ser. No. 09/765,874, filed Jan. 19, 2001; and Ser. No. 09/767,579, filed Jan. 22, 2001.

In some configurations, the selectable emission filter could be changed rapidly, for example, at the 10–20 Hz pulse rate of the excitation laser, or at slower rates of 10 to 0.1 Hz, to permit ratiometric analysis of light emitted at two or more wavelengths. Similarly the excitation wavelengths could be changed rapidly to provide ratiometric analysis of emission light from excitation at two or more wavelengths. Lastly, combinations of excitation and emission ratiometric analysis could be performed, where two or more excitation wavelengths are used, and where each of the excitation wavelengths is monitored for emission of fluorescence light at two or more emission wavelengths.

III. EXAMPLES

The following examples describe selected aspects and embodiments of the invention, including exemplary optical components, shot-to-shot light uniformity, cross-plate light uniformity, adequacy of illumination power, cell photobleaching, undiffracted central spot, scattered/wasted light, diffractive efficiency, and laser damage to the diffractive optic, among others. These examples are included for illustration and are not intended to limit or define the entire scope of the invention.

EXAMPLE 1

Construction of Prototype Apparatus

Figure 2:
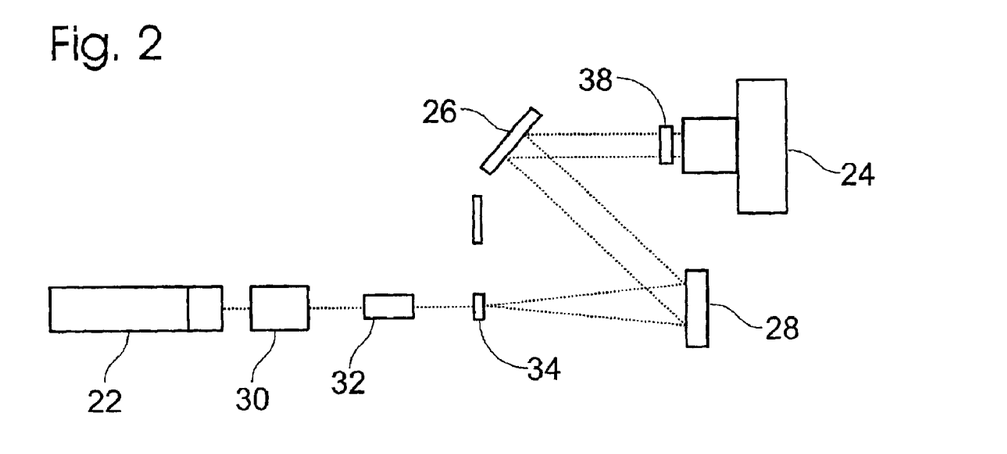
FIG. 2 is a schematic side view of an alternative light detection device, constructed in accordance with aspects of the invention, also as described in Example 1. The device is capable of optical illumination and/or detection.

This example, illustrated in FIGS. 1 and 2, describes two alternative apparatuses constructed in accordance with aspects of the invention. The apparatuses each include a light source, a wavelength converter, an optical pattern generator, a detector, and an optical relay structure adapted to transmit light to and/or from these optical elements and an examination site.

The light source and wavelength converter includes a pulsed YAG laser (1060 nm) with harmonic generators that created a third harmonic at 353 nm and a CONTINUUM SURELITE II Optical Parametric Oscillator, which is pumped by the YAG laser. The OPO has a micrometer knob and a look-up table allowing selection of any wavelength from 400–2500 nm.

The optical pattern generator includes a diffractive optic (commercially available from Edmund Scientific) that produces an 8×8 array of beamlets from the single incoming beam. The divergence angle of the exit beamlets is dependent on the wavelength of light.

The detector includes a ROPER SCIENTIFIC QUANTIX 57 back-illuminated, frame-transfer CCD camera detector, which can be focused on the bottom surface of a microplate to record a fluorescence signal. For most experiments, an excitation wavelength of 488 nm is used, and a standard fluorescence long-pass filter is placed in front of the camera to exclude the excitation light.

The optical relay structure includes various mirrors and lenses. For example, light leaving the OPO is too divergent for efficient use with a binary optic, so a telescopic beam expander is used to recollimate the beam and fill the optic. The apparatus was used in two different optical configurations with three different target plates. In one configuration, shown in FIG. 1, the horizontal beam exiting the diffractive optic was reflected off a plane mirror and intercepted by a (horizontal) multiwell microplate. In an alternative configuration, shown in FIG. 2, the laser was aimed directly at the microplate.

Experiments were performed under the following conditions: (1) excitation laser pulses triggered either internally (at a repetition rate of 5–11 Hz) or externally; (2) a 50-mm lens, with an f2 aperture setting and a 50-ms exposure time; and (3) laser excitation at 488 nm, 1.49 kV, with 192 $\mu$s q-switch delay (maximum power output).

EXAMPLE 2

Analysis of Illumination Power and Uniformity Across a Microplate

Figures 3, 3A:
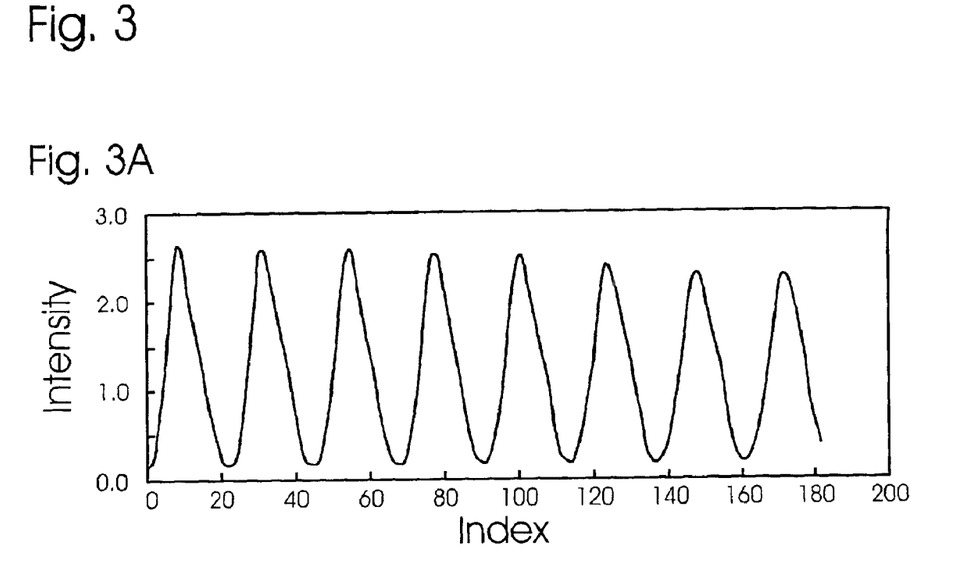
FIG. 3 shows the fluorescence intensity across a calibration microplate when illuminated by an illumination apparatus of the invention, as described in Example 2.
FIG. 3A is a plot of fluorescence intensity versus position scanned through a horizontal line across a row of the calibration microplate.

This example, illustrated in FIG. 3, describes the analysis of illumination power and uniformity across a microplate.

The power and uniformity of illumination produced by the apparatus were determined using a standard 384-well calibration microplate, i.e., a multiwell microplate that had been coated with a uniform layer of fluorescein. The illumination laser was run at maximum power output, internally triggered at a pulse rate of 10 Hz. The average power out of the OPO was measured at 250 mW, or about 25 mJ/pulse. The time-averaged illumination intensity was calculated to be approximately 0.22 mW/mm$^2$, by considering the illuminated area to be approximately 1200 mm$^2$ (calculated as the sum of the cross-sectional areas of all of the microplate wells, i.e., $\pi \times (1 \text{ mm})^2 \times 384$).

Figure 3B:
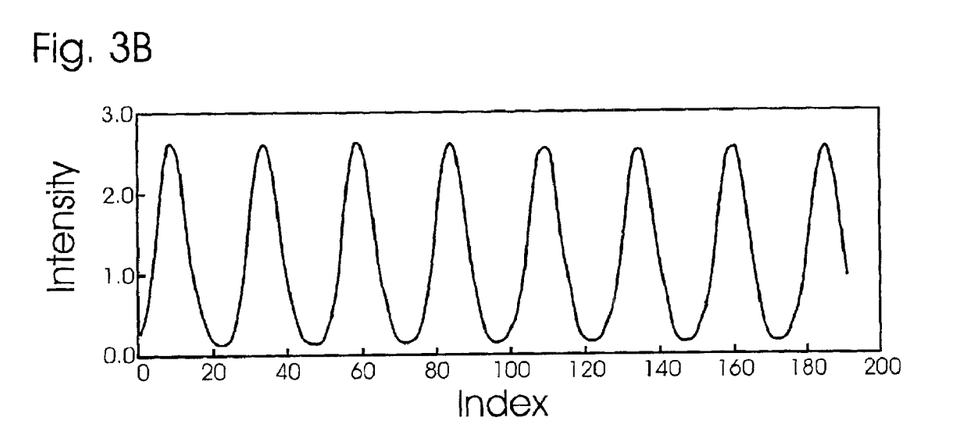
FIG. 3B is a plot of fluorescence intensity versus position scanned down a vertical line across a column of the calibration microplate.

The fluorescence of the calibration microplate was analyzed by recording and analyzing a series of exposures. Specifically, fluorescence emission intensity was determined by recording a linear scan across a row of microplate wells, as shown in FIG. 3A, and a linear scan down a column of microplate wells, as shown in FIG. 3B.

The results provide an indication of the maximum power of the illuminating laser at the excitation wavelength used. As shown by the uniform fluorescence intensity across individual microplate wells, the laser beamlets provided by the diffractive optic had a substantially uniform power distribution across the microplate. A custom diffractive optic, rather than the commercially available diffractive optic used, could render the light distribution across each well more uniform, producing an intensity profile having flatter-topped intensity peaks.

EXAMPLE 3

Laser Triggering

Figure 4:
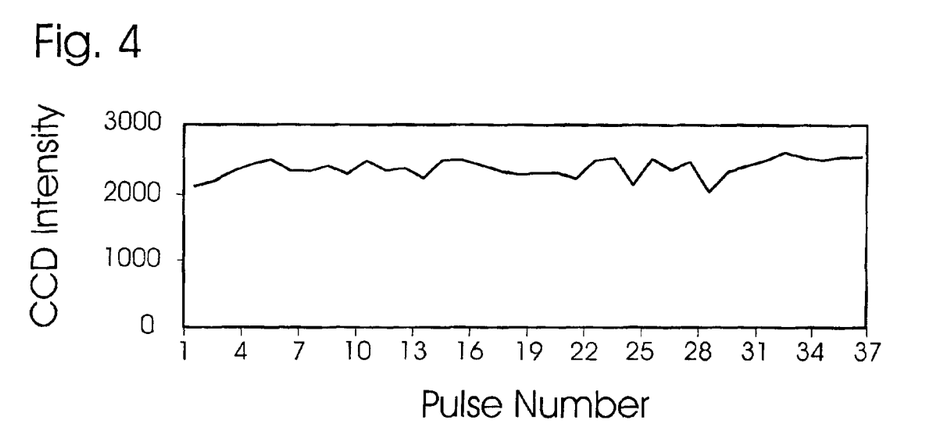
FIG. 4 is a plot of CCD intensity versus pulse number showing the pulse-to-pulse variations in illumination laser intensity of an apparatus of the invention when the laser is internally triggered, as described in Example 3.
Figure 5:
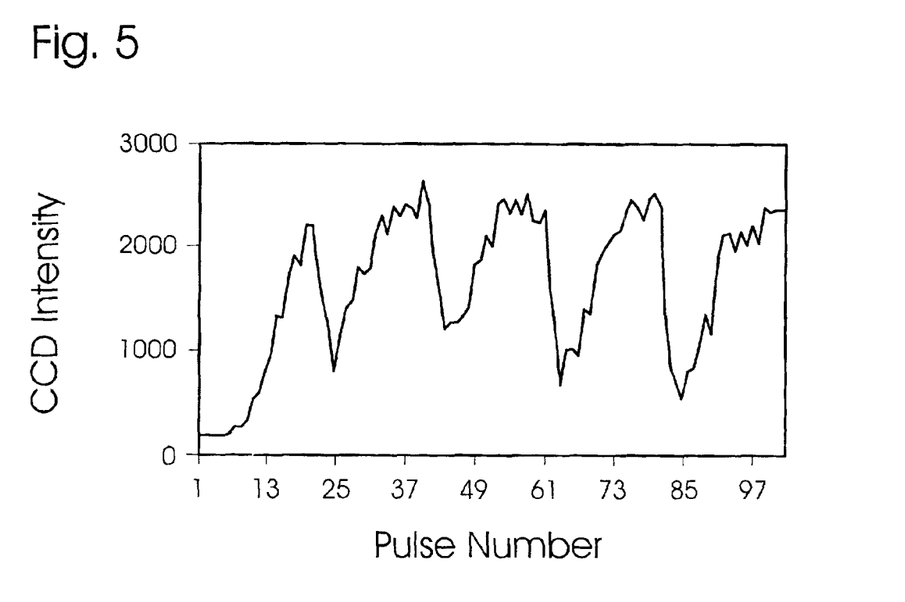
FIG. 5 is a plot of CCD intensity versus pulse number showing the pulse-to-pulse variations in illumination laser intensity of an apparatus of the invention when the laser is externally triggered, by the camera, also as described in Example 3.

This example, illustrated in FIGS. 4 and 5, describes laser (and camera) triggering.

The illumination laser was utilized in several different operational modes. For the particular laser used in these experiments, the power output and shot-to-shot consistency were maximized when the laser was triggered internally, with the flash lamps firing at a predetermined steady rate close to about 10 Hz. This firing mode produced relatively consistent laser pulse intensity, as shown in FIG. 4. The coefficient of variance of the pulse intensity data in this case was about 142/2500, or about 0.057, computed as the standard deviation in the measured results divided by the associated mean. In some experiments, due to idiosyncrasies of the experimental set up, the laser was not triggered internally, but instead was triggered externally from the camera by using the "shutter open" signal. This trigger protocol insured that the laser fired while the shutter was open, resulting in a consistent period for the laser pulses.

The camera was programmed to take frames at a rate of approximately 10 Hz. However, the laser did not reach full power during the initial pulses of a series, so to allow the laser to reach maximum power, 20 frames were taken in a series. This process was repeated 5 times to produce the data shown in FIG. 5, which shows a rapid rise in laser pulse energy over the course of the 20 shots and a sharp drop in laser pulse energy during the period (approximately 200 ms) between pulse series.

Various mechanisms may be used to compensate for variations in pulse energy during pulse series. For example, in cell-based experiments, the variation in pulse intensity was compensated for by recording only the final shot of each series of twenty pulses. Alternatively, the laser could be internally triggered in a continuous pulse mode (10 Hz), and the camera could be triggered from the laser with an appropriate delay to record data at a selected rate, for example, in 100-ms increments.

EXAMPLE 4

Sensitivity and Dynamic Range

This example describes measurements of sensitivity and dynamic range. In particular, the sensitivity and dynamic range measured using the diffractive setup described above described above were comparable to those measured using a FLIPR fluorometric imaging plate reader system (Molecular Devices Corporation). By illuminating with diffractive optics of the apparatus, two decades of dynamic range were obtained, as opposed to (barely) three decades of dynamic range observed with the continuous wave laser. In decade plate experiments (utilizing serial dilutions of fluorescein in a 384-well microplate), fluorescein concentrations as low as $10^{-7}$ were easily detectable with either system. Fluorescein concentrations of $10^{-8}$ could be detected with longer exposures and continuous illumination. Additional improvements in sensitivity could be achieved by using multiple excitation pulses per exposure and/or opening up the aperture of the camera lens.

EXAMPLE 5

Cell-Based Experiments

This example describes considerations for conducting cell-based experiments.

The analysis of cell-based samples, typically by monitoring dynamic reactions, was facilitated by collecting data at known, regular intervals. The illumination laser was set to trigger from the CCD camera, as described above. Consistency and maximal power were achieved by programming the camera to take a series of 20 frames in a row, thereby bringing the laser up to full power, but saving the data from only the last shot of the series, also as described above. This programming strategy effectively reduced data flow, so that computer resources were not strained by data processing. The end result was one frame of data being saved approximately every two seconds. Better electronics integration and more effective triggering and/or data capture routines should allow data capture rates (with full laser power) of up to at least about 10 Hz with currently available technology.

EXAMPLE 6

Calcium Flux Assay

Figure 6A:
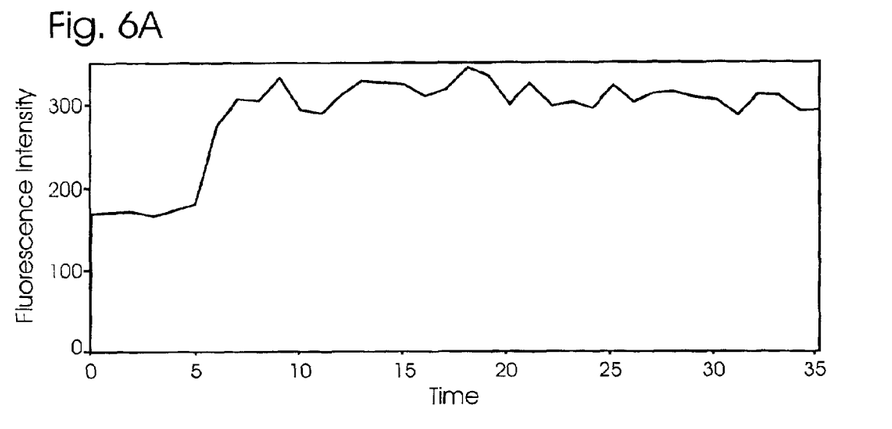
FIG. 6A is a plot of fluorescence intensity versus time showing average fluorescence intensity in a single selected well as a function of time after addition of carbachol.
Figure 6B:
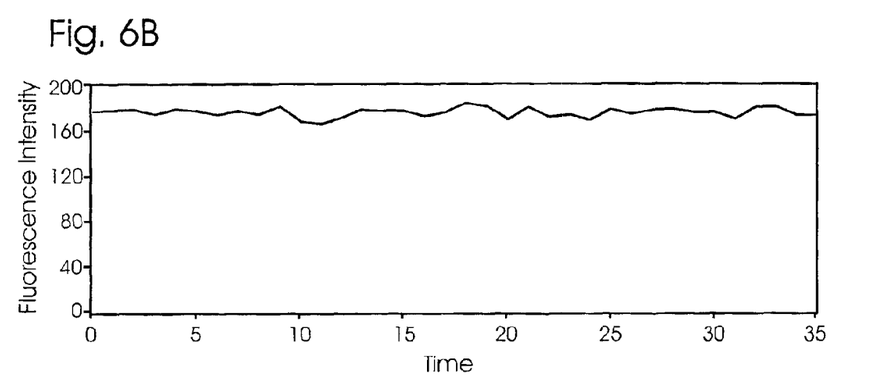
FIG. 6B is a plot of fluorescence intensity versus time showing average fluorescence intensity in a single selected well as a function of time in the absence of added carbachol.
Figure 7:
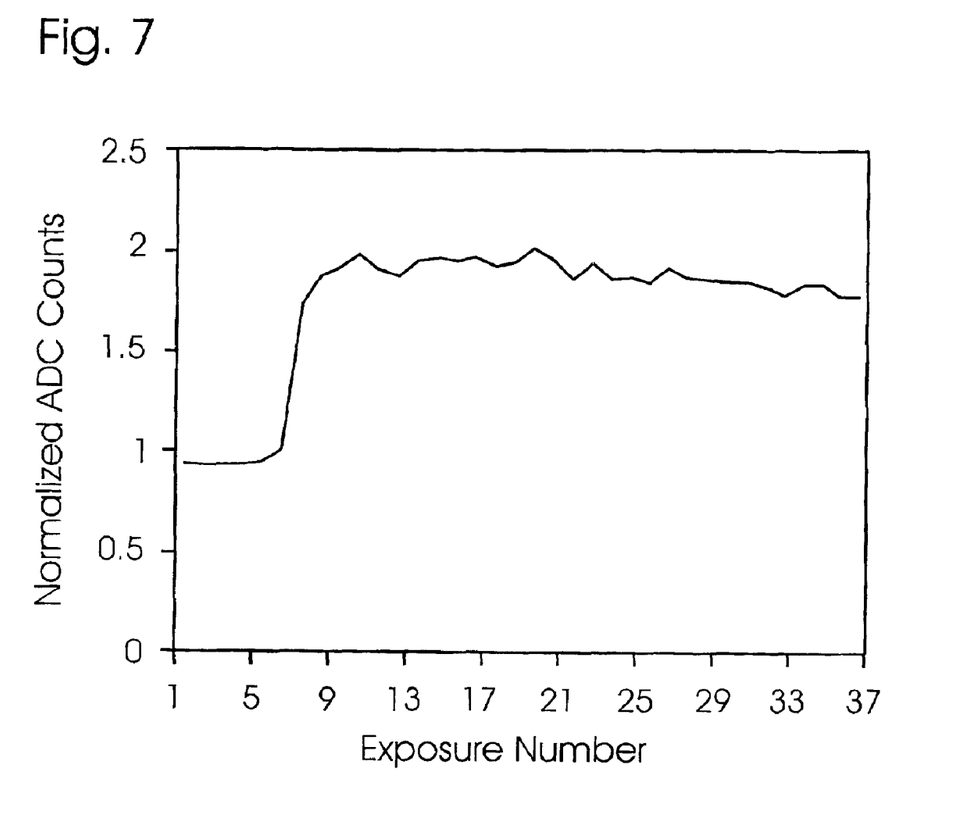
FIG. 7 is a plot of normalized fluorescence versus exposure time showing average fluorescence intensity upon addition of carbachol, where the data have been normalized with respect to the fluorescence intensity observed in a well in which no carbachol was added.

This example, illustrated in FIGS. 6 and 7, describes calcium flux assays conducted using an apparatus constructed in accordance with aspects of the invention.

Cultured CHO m1 cells were grown overnight in a 384-well microplate, then loaded with a cell-permeant form of a fluorescent calcium ion indicator for 1 hour. The fluorescent form of the calcium indicator exhibits excitation and emission wavelengths of approximately 495 nm and 525 nm, respectively. The manual addition of carbachol (a calcium flux stimulant) in 10 nM, 100 nM, and 10 $\mu$M concentrations was used to mimic small, medium, and large sustained responses.

FIG. 6A shows the results of the addition of carbachol to the cell samples. There was a rapid increase in the fluorescence signal over the first few frames, with a slow decay over the remaining duration of the experiment. The figure records the average light intensity in a single selected well as a function of frame number (each frame taken approximately two seconds apart), where the selected well was one to which carbachol was added.

FIG. 6B shows a similar graph of average intensity for a noncarbachol stimulated well. Here, no sustained increase in signal strength was observed, although there were small fluctuations due to shot-to-shot variations in illumination laser intensity. Careful observation revealed similar fluctuations in FIG. 6A, suggesting normalizing the data against the intensity of a control well and/or some other indicator of laser pulse intensity may be a useful method for reducing noise in the carbachol signal.

FIG. 7 shows how, by dividing the fluorescence counts from wells to which carbachol was added by the fluorescence counts from a nearby well to which no carbachol was added, a set of normalized data may be obtained that is significantly smoother.

The measurements depicted in FIGS. 6 and 7 were repeated for four different samples. The average signal-to-noise ratio for the raw data was about 10.2, while the average signal-to-noise ratio for the normalized data was about 18.8.

The experimental data also are significant in that no evidence of photobleaching was observed. This observation supports calculations suggesting that photobleaching effects would not be worse with a pulsed laser than with a continuous wave laser, at comparable average power levels.

The disclosure set forth above may encompass multiple distinct inventions with independent utility. Although each of these inventions has been disclosed in its preferred form, the specific embodiments thereof as disclosed and illustrated herein should not to be considered in a limiting sense as numerous variations are possible. For example, instead of using a diffractive optic, a beam expander or a pair of crossed cylindrical lenses may be used to broaden and shape the laser beam to fill the entire surface of a sample substrate such as a microplate. Similarly, the diffractive optic approach to beam delivery may be applied with a continuous wave laser. The subject matter of the inventions includes all novel and nonobvious combinations and subcombinations of the various elements, features, functions and/or properties disclosed herein. It is believed that the following claims particularly point out certain combinations and subcombinations that are directed to one of the disclosed inventions and are novel and nonobvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

We claim:

1. A light detection device, comprising:

a light source configured to produce light of a first wavelength;

a wavelength converter configured to receive the light of the first wavelength and to convert that light into light of a second wavelength, where the second wavelength is different than the first wavelength;

a system for directing the light of the second wavelength to an examination area, wherein a sample holder comprising a plurality of sample sites is positioned in the examination area; and a detector configured to receive luminescence light from samples positioned in the plurality of sample sites, wherein the system for directing light includes:

an optical pattern generator configured to convert the light of the second wavelength into light having a preselected intensity pattern, and an optical relay structure configured to project the light having the preselected pattern onto the examination area, where the projected pattern substantially conforms to the arrangement of sample sites in at least a portion of the sample holder, where the light source is a pulsed laser, where the pulsed laser is triggered by the detector.

2. A light detection device, comprising:

a light source configured to produce light of a first wavelength;

a wavelength converter configured to receive the light of the first wavelength and to convert that light into light of a second wavelength where the second wavelength is different than the first wavelength;

a system for directing the light of the second wavelength to an examination area, wherein a sample holder comprising a plurality of sample sites is positioned in the examination area; and a detector configured to receive luminescence light from samples positioned in the plurality of sample sites, wherein the system for directing light includes:

an optical pattern generator configured to convert the light of the second wavelength into light having a preselected intensity pattern, and an optical relay structure configured to project the light having the preselected pattern onto the examination area, where the projected pattern substantially conforms to the arrangement of sample sites in at least a portion of the sample holder, where the wavelength converter converts the light of the first wavelength into the light of the second wavelength and light of a third wavelength, where the energy associated with a photon of the light of the first, wavelength substantially equals the sum of the energies associated with a photon of light of the second wavelength and a photon of light of the third wavelength.

3. A light detection device, comprising:
   a light source configured to produce light of a first wavelength;
   a wavelength converter configured to receive the light of the first wavelength and to convert that light into light of a second wavelength, where the second wavelength is different than the first wavelength;
   a system for directing the light of the second wavelength to an examination area, wherein a sample holder comprising a plurality of sample sites is positioned in the examination area; and
   a detector configured to receive luminescence light from samples positioned in the plurality of sample sites,
   wherein the system for directing light include:
   an optical pattern generator configured to convert the light of the second wavelength into light having a preselected intensity pattern, and
   an optical relay structure configured to project the light having the preselected pattern onto the examination area, where the projected pattern substantially conforms to the arrangement of sample sites in at least a portion of the sample holder,
   the device further comprising a wavelength selector configured to adjust the wavelength converter to select the second wavelength,
   where the wavelength selector operates by changing the relative angle between the light of the first wavelength and a portion of the wavelength converter.

4. The device of claim 3, where the wavelength selector automatically changes the relative angle between the light of the first wavelength and a portion of the wavelength converter.

5. The device of claim 3, where the wavelength selector changes the relative angle between the light of the first wavelength and a portion of the wavelength converter in a continuous fashion.

6. A light detection device comprising:
   a light source configured to produce light of a first wavelength;
   a wavelength converter configured to receive the light of the first wavelength and to convert that light into light of a second wavelength, where the second wavelength is different than the first wavelength;
   a system for directing the light of the second wavelength to an examination area, wherein a sample holder comprising a plurality of sample sites is positioned in the examination area; and
   detector configured to receive luminescence light from sample positioned in the plurality of sample sites,
   wherein the system for directing light includes:
   an optical pattern generator configured to convert the light of the second wavelength into light having a preselected intensity pattern, and
   an optical relay structure configured to project the light having the preselected pattern onto the examination area, where the projected pattern substantially conforms to the arrangement of sample sites in at least a portion of the sample holder,
   the device further comprising a fluid delivery system that includes a dispensing device configured to deliver a fluid material to the sample,
   where the detector is configured to coordinate the reception of luminescence light from the sample with the delivery of the fluid material to the sample.

7. A method of detecting light transmitted from a sample, comprising:
   outputting light from a light source, the light having a first wavelength;
   selectively converting the light having the first wavelength to light having a second wavelength, where the second wavelength is different than the first wavelength;
   directing the light having the second wavelength onto a plurality of samples positioned in a sample holder; and
   measuring light transmitted from the samples induced by the light having the second wavelength,
   wherein the step of directing the light having the second wavelength onto the samples comprises converting the light into light having a preselected intensity pattern and projecting the light having the preselected pattern onto the sample holder, where the projected pattern substantially conforms to the arrangement of samples in at least a portion of the sample holder,
   where the step of selectively converting includes the step of converting the light having the first wavelength to light having the second wavelength and light having a third wavelength,
   further comprising the step of discarding the light of the third wavelength.

8. A method of detecting light transmitted from a sample, comprising:
   outputting light from a light source, the light having a first wavelength;
   selectively converting the light having the first wavelength to light having a second wavelength, where the second wavelength is different than the first wavelength;
   directing the light having the second wavelength onto a plurality of samples positioned in a sample holder; and
   measuring light transmitted from the sample induced by the light having the second wavelength,
   wherein the step of directing the light having the second wavelength onto the samples comprises converting the light into light having a preselected intensity pattern and projecting the light having the preselected pattern onto the sample holder, where the projected pattern substantially conforms to the arrangement of samples in at least a portion of the sample holder,
   further comprising the step of exposing the sample to an electrical potential selected to stimulate one or more sample components.

9. A method of detecting luminescence from a luminescent sample, comprising:
   outputting light from a light source, the light being capable of inducing luminescence in the sample;
   selectively converting the light into light having a preselected intensity pattern;
   directing the light having the preselected intensity pattern onto a sample holder so that the light is incident at least substantially only on Sample sites in the sample holder; and
   measuring luminescence light transmitted from at least one of the sample sites induced by the light having the preselected intensity pattern,
   said method further comprising:
   exposing the sample to a reagent or an environmental condition;
   incubating the sample for a time sufficient for the reagent or environmental condition to detectably effect the sample;

directing the light having the preselected intensity pattern onto the sample holder;

measuring the luminescence light transmitted from at least one of the sample sites induced by the light having the preselected intensity pattern; and comparing the luminescence light transmitted from at least one of the sample sites with the luminescence light transmitted from the same sample site before the step of exposing the sample to the reagent or the environmental condition.

10. The method of claim 9, where the luminescence light transmitted from each of the sample sites is compared with the luminescence light transmitted from that sample site before the step of exposing the sample to the reagent or the environmental condition.

11. A light detection device, comprising:
a pulsed laser configured to produce light of a first wavelength;
a wavelength converter configured to receive the light of the first wavelength and to convert that light into light of a second wavelength, where the second wavelength is different than the first wavelength;
a system for directing the light of wavelength to an examination area; and
a detector configured to receive luminescence light from a sample positioned in the examination area, wherein the pulsed laser is triggered by the detector.

12. A light detection device, comprising:
a light source configured to produce light of a first wavelength;
a wavelength converter configured to receive the light of the first wavelength and to convert that light into light of a second wavelength, where the second wavelength is different than the first wavelength;
a system for directing the light of the second wavelength to an examination area; and
a detector configured to receive luminescence light from a sample positioned in the examination area,
wherein the wavelength converter converts the light of the first wavelength into the light of the second wavelength and light of a third wavelength, and wherein the energy associated with a photon of the light of the first wavelength substantially equals the sum of the energies associated with a photon of light of the second wavelength and a photon of light of the third wavelength.

13. A light detection device, comprising:
a light source configured to produce light of a first wavelength;
a wavelength converter configured to receive the light of the first wavelength and to convert that light into light of a second wavelength, where the second wavelength is different than the first wavelength;
a wavelength selector configured to adjust the wavelength converter to select the second wavelength;
a system for directing the light of the second wavelength to an examination area; and a detector configured to receive luminescence light from a sample positioned in the examination area wherein the wavelength selector operates by changing the relative angle between the light of the first wavelength and a portion of the wavelength converter.

14. The device of claim 13, where the wavelength selector automatically changes the relative angle between the light of the first wavelength and a portion of the wavelength converter.

15. The device of claim 13, where the wavelength selector changes the relative angle between the light of the first wavelength and a portion of the wavelength converter in a continuous fashion.

16. A method of detecting light transmitted from a sample, comprising:
outputting light from a light source, the light having a first wavelength;
selectively converting the light having the first wavelength to light having a second-wavelength, where the second wavelength is different than the first wavelength;
directing the light having the second wavelength onto the sample;
exposing the sample to an electrical potential selected to stimulate one or more sample components; and
measuring light transmitted from the sample induced by the light having the second wavelength.

17. A method of detecting luminescence from a luminescent sample, comprising:
outputting light from a light source, the light being capable of inducing luminescent the sample;
selectively converting the light into light having a preselected intensity pattern;
exposing a sample to a reagent or an environmental condition;
incubating the sample for a time sufficient for the reagent or environmental condition to detectably effect the sample;
directing the light having the preselected intensity pattern onto a sample holder so that the light is incident at least substantially only on sample sites in the sample holder;
measuring luminescence light transmitted from at learnt one of the sample sites induced by the light having the preselected intensity pattern; and
comprising the luminescence light transmitted from at least one of the sample sites with the luminescence light transmitted from the same sample site before the step of exposing the sample to the reagent or the environmental condition.

18. The method of claim 16, where the luminescence light transmitted from each of the sample sites is compared with the luminescence light transmitted from that sample site before the step of exposing the sample to the reagent or the environmental condition.

* * * * *

UNITED STATES PATENT AND TRADEMARK OFFICE
CERTIFICATE OF CORRECTION

PATENT NO. : 6,930,314 B2  
DATED : August 16, 2005  
INVENTOR(S) : Joseph H. Jackson III et al.

It is certified that error appears in the above-identified patent and that said Letters Patent is hereby corrected as shown below:

Column 20,  
Line 56, change "Sample" to -- sample --.

Column 22,  
Line 33, change "luminescent the sample" to -- luminescence in the sample --.  
Line 45, change "learnt" to -- least --.

Signed and Sealed this

Eighteenth Day of October, 2005

JON W. DUDAS  
*Director of the United States Patent and Trademark Office*